(12) United States Patent
Maegawa

(10) Patent No.: US 8,975,298 B2
(45) Date of Patent: Mar. 10, 2015

(54) THERAPEUTIC AGENT FOR PAIN

(75) Inventor: Hitoshi Maegawa, Osaka (JP)

(73) Assignee: ONO Pharmaceutical Co., Ltd., Osaka (JP)

( * ) Notice: Subject to any disclaimer, the term of this patent is extended or adjusted under 35 U.S.C. 154(b) by 372 days.

(21) Appl. No.: 11/993,979

(22) PCT Filed: Jun. 26, 2006

(86) PCT No.: PCT/JP2006/312712
§ 371 (c)(1),
(2), (4) Date: Dec. 27, 2007

(87) PCT Pub. No.: WO2007/000970
PCT Pub. Date: Jan. 4, 2007

(65) Prior Publication Data
US 2009/0030078 A1      Jan. 29, 2009

(30) Foreign Application Priority Data
Jun. 27, 2005   (JP) ................................ 2005-185916

(51) Int. Cl.
*A61K 31/20* (2006.01)
*A61K 31/00* (2006.01)
*A61K 45/06* (2006.01)

(52) U.S. Cl.
CPC ................. *A61K 31/00* (2013.01); *A61K 31/20* (2013.01); *A61K 45/06* (2013.01)
USPC ........................................................ 514/558

(58) Field of Classification Search
None
See application file for complete search history.

(56) References Cited

U.S. PATENT DOCUMENTS

| | | |
|---|---|---|
| 6,187,338 B1 | 2/2001 | Caruso et al. |
| 6,201,021 B1 | 3/2001 | Ohuchida et al. |
| 6,406,716 B2 | 6/2002 | Caruso et al. |
| 2001/0008889 A1 | 7/2001 | Caruso et al. |
| 2003/0096802 A1 | 5/2003 | Ohuchida et al. |
| 2004/0235949 A1 | 11/2004 | Kozak et al. |
| 2005/0261371 A1 | 11/2005 | Ohuchida et al. |
| 2005/0267167 A1 | 12/2005 | Ohuchida et al. |
| 2005/0267168 A1 | 12/2005 | Ohuchida et al. |

FOREIGN PATENT DOCUMENTS

| | | | |
|---|---|---|---|
| JP | 07-316092 | 12/1995 | |
| JP | 2001-500121 | 1/2001 | |
| JP | 2001-509500 A | 7/2001 | |
| JP | 2005-500305 | 1/2003 | |
| WO | 99/02485 | 1/1999 | |
| WO | 03/000173 | 1/2003 | |
| WO | WO 2004/110972 | * 12/2004 | ............ C07C 231/06 |
| WO | WO 2005/032537 | * 4/2005 | ............ A61K 31/20 |

OTHER PUBLICATIONS

Stella et al (Prodrugs: Challenges and Rewards, Part 1, 2007).*
Galloway (OncoLog 49, May 2004).*
Tanga et al (Nuerochem Int 45:397-407, 2004).*
Honore et al (Neuroscience 98:585-598, 2000).*
Tateishi et al (J Cereb Blood Flow and Metab 22:723-734, 2002).*
Shanmugam et al (J Biol Chem 278:34834-34844, 2003).*
Sabino et al (Cancer Res 62:7343-7349, 2002).*
Suyama et al (Brain Res 1010:144-150, 2004—Abstract only).*
L.A. Sorbera et al., "Astrocyte-Modulating Agent Treatment of Stroke Treatment of Neurodegeneration", Drugs of the Future, 2004, pp. 441-448, vol. 29, No. 5, Prous Science.
Takashi Mori et al., "Attenuation of a delayed increase in the extracellular glutamate level in the peri-infarct area following focal cerebral ischemia by a novel agent ONO-2506", Neurochemistry International, 2004, pp. 381-387, vol. 45, Elsevier Ltd.
Takao Asano et al., "Functional modulation of astrocytes by a novel agent ONO-2506 mitigates delayed infarct expansion with a wide therapeutic time window, inducing prompt neurological recovery through reduction of the extracellular level of glutamate", International Congress Series, 2003, pp. 147-151, vol. 1252, Elsevier Science B.V.
Takaomi Taira et al., "Shinkei Insei Totsu no Kijo", Igaku no Ayumi, 1999, pp. 751-755, vol. 189, No. 10.
Takahiro Suzuki et al., "Rinsho to Yakubutsu Chiryo", 1999, pp. 643-646, vol. 18, No. 7.
Extended European Search Report dated Dec. 10, 2009.
European Patent Office, Communication pursuant to Article 94(3) EPC, issued Nov. 18, 2011 in corresponding European Patent Application No. 06 767 329.3.
Japanese Patent Office, Office Action dated May 17, 2012 issued in a corresponding Japanese application No. 2007-523928.
Japan Patent Office, Communication issued on Mar. 1, 2012, in a counterpart Japanese Application No. 2007-523928.
European Patent Office, Extended European Search Report dated Jan. 10, 2013, issued in corresponding European Patent Application No. 12001669.6.

* cited by examiner

*Primary Examiner* — Craig Ricci
(74) *Attorney, Agent, or Firm* — Sughrue Mion, PLLC

(57) ABSTRACT

The present invention relates to an agent for prevention, treatment or inhibition of symptom progression of a pain and/or for control of an analgesic comprising (2R)-2-propyloctanoic acid, a salt thereof or a prodrug thereof, in which an amount per dose is from 1 mg to 5000 mg (preferably from 10 mg to 5000 mg). By administering (2R)-2-propyloctanoic acid, a salt thereof or a prodrug thereof in an amount per dose within the range as described above, a pain, in particular, a neurogenic pain associated with a disease such as cancer pain, postherpetic pain, diabetic pain, HIV-associated neurogenic pain, calculus-induced pain, neuralgia, orofacial pain or hyperalgesia can be remarkably relieved. Moreover, undesirable effects on the living body relating to the use of an analgesic can be relieved.

7 Claims, No Drawings

THERAPEUTIC AGENT FOR PAIN

This is a national stage application under 35 U.S.C. 371 of PCT/JP2006/312712 filed on Jun. 26, 2006, which claims priority from Japanese patent application 2005-185916 filed on Jun. 27, 2005, all of which are incorporated herein be reference.

TECHNICAL FIELD

The present invention relates to an agent for prevention, treatment or inhibition of symptom progression of a pain and/or for control of an analgesic comprising (2R)-2-propyloctanoic acid, a salt thereof or a prodrug thereof, and the like.

BACKGROUND ART

According to *Classification of Chronic Pain* published by International Association for the Study of Pain (IASP) in 1994, "pain" is defined as "an unpleasant sensory and emotional experience associated with actual or potential tissue damage, or described in terms such damage".

Pain is mainly classified into (1) "nociceptive pain" seemingly caused by continuous stimulation of nociceptors; (2) "neurogenic pain" caused by a dysfunction in nerve fibers participating in the mechanism of transmitting and/or suppressing pain; and (3) "psychogenic pain" focusing on emotional and/or affective points.

Among these pains, neurogenic pain is an intractable pain which arises as the results of a dysfunction in the peripheral or central nerve system. It is considered that neurogenic pain is caused by, for example, compression, a trauma or an injury of peripheral nerve, a nerve plexus or a perineural soft tissue, or a damage in a central somatosensory pathway (for example, an ascending somatosensory pathway at the level of spinal cord, brain stem, thalamus or cortex) and so forth. More specifically, it might be induced by a neurodegenerative disease, an oseteodegenerative disease, a metabolic error (for example, diabetes), cancer, infection, inflammation, ischemia, a surgical operation, trauma, radiotherapy, the administration of an anticancer agent and so forth.

Although the mechanism of neurogenic pain onset still remains unknown in many points, it is assumed that the mechanism comprises spontaneous firing in sensory nerve caused by a newly expressed ion channel of a certain type, protrusion of sensory nerve fibers into various layers of the spinal cord, and changes in the expression of various neurotransmitters and receptors in the sensory nerve and spinal cord. Typical symptoms of neurogenic pain include allodynia, hyperalgesia, hyperesthesia and the like. These symptoms present characteristic pains just like as "burned", "pinpricked", "getting an electrical shock", etc. It has been known that neurogenic pain can be hardly overcome not only by using analgesics which are effective on common nociceptive pain but also even by using narcotic analgesics (*The Lancet*, 353, 1959-1966, 1999). For example, it is known that morphine, which has a potent analgesic effect on nocuous pain, shows only an insufficient effect on neurogenic pain. Since the insufficient analgesic effect of morphine is large feature of neurogenic pain, it is used in diagnosing neurogenic pain (*Igaku no Ayumi*, 189(10), 751-755, 1999). It is considered that the reason for the non-effectiveness of morphine on neurogenic pain is the denaturation of inhibitory neurons or a decrease in opioid receptors due to functional or morphological changes caused by neuropathy (*Saishin Nou to Shinkeikagaku Sirizu*, vol. 6, *Itami no Shinkeikagaku*, published by Medical View, 97, 1997).

As described above, allodynia is one of the typical symptoms of neurogenic pain. Allodynia means a state of suffering from a pain due to a stimulus which does not provoke any pain in normal people. In allodynia, even a non-noxious stimulus such as a light touch or compression, or moderate cold or warmth induces a pain. Namely, the fundamental characteristics of allodynia are that having a qualitative conversion of sensory response and the threshold thereof per se is lowered. In postherpetic neuralgia that is a typical example of neurogenic pain, allodynia is observed in 87% of patients and it is reported that the pain level in postherpetic neuralgia is proportional to the severity of allodynia. Since allodynia is a symptom which seriously decreases the QOL of patients with neurogenic pain including postherpetic neuralgia, it has attracted public attention as a highly important subject to be treated.

As a method for treating neurogenic pain, neurosurgical therapies such as nerve block and spinal epidural electrical stimulus (*Igaku no Ayumi*, 189(10), 757-762, 1999), gabapentinoids such as gabapentin and pregabalin, N-type calcium channel inhibitors such as ziconotide, tricyclic antidepressants (*Rinsho to Yakubutsu Chiryo*, 18(7), 643-646, 1999), antiepileptics, local anesthetics, baclofen and so forth are used. However, no safe and efficacious therapeutic method has been established yet. Therefore, it has been urgently required to develop a therapeutic agent which is effective for neurogenic pain.

On the other hand, it is reported that (2R)-2-propyloctanoic acid is a compound which can improve the function of abnormally activated astrocytes and can be used as an agent for prevention or treatment of various cranial nerve diseases including cerebral stroke since it has an effect of reducing intracellular $S100\beta$ content (see, for example, *Journal of cerebral blood flow & metabolism*, 22(6), 723-734, 2002: Non-Patent Document 1).

It is also known that pentanoic acid derivatives including (2R)-2-propyloctanoic acid have an effect of improving the function of astrocytes and are useful as an agent for improving brain function. For example, they can be used in treatment of Alzheimer's disease, amyotrophic lateral sclerosis, neurological dysfunction of cerebral stroke or brain injury and so forth. Concerning dosing, it is reported that such a compound is orally administered to an adult in an amount per dose of from 1 to 1000 mg once to several times per day, or parenterally administered in an amount per dose of from 0.1 to 100 mg once to several times per day (see, for example, the specification of European Patent 0632008; Patent Document 1).

However, it has never been reported so far that (2R)-2-propyloctanoic acid is useful against a pain, in particular, a neurogenic pain.

[Non-Patent Document 1] *Journal of cerebral blood flow & metabolism*, 22(6), 723-734, 2002

[Patent Document 1] specification of European Patent

DISCLOSURE OF THE INVENTION

Problems to be Solved by the Invention

An object of the present invention is to provide an agent for prevention, treatment or inhibition of symptom progression of a pain, in particular, a neurogenic pain which is highly safe and is useful as a medicine and to provide a specific method of administering the same.

Means for Solving the Problems

As the results of studies with the use of rat lumbar nerve ligation models, the inventors of the present invention found out that (2R)-2-propyloctanoic acid showed a surprising effect of inhibiting a pain caused by the nerve ligation, i.e., heat hyperalgesia and contact allodynia when orally it is administered in an amount per dose of 30 mg/kg once a day for 14 days immediately after the nerve ligation. Based on the finding, the inventors of the present invention further conducted studies and found out that (2R)-2-propyloctanoic acid is also usable in controlling an analgesic to accomplish the present invention.

Accordingly, the present invention relates to:

[1] An agent for prevention, treatment or inhibition of progression of a pain and/or for control of an analgesic comprising (2R)-2-propyloctanoic acid, a salt thereof or a prodrug thereof;
[2] The agent according to [1], wherein the amount per dose is from 10 mg to 5000 mg;
[3] The agent according to [2], which is for oral administration;
[4] The agent according to [3], wherein the amount per dose in the oral administration is from 100 mg to 5000 mg;
[5] The agent according to [2], which is for parenteral administration;
[6] The agent according to [5], wherein the parenteral administration is intravenous administration;
[7] The agent according to [6], wherein the amount per dose in the intravenous administration is from 100 mg to 2000 mg;
[8] The agent according to [6], wherein the amount per dose in the intravenous administration is from 2 mg to 20 mg per 1 kg of body weight;
[9] The agent according to [6], wherein the intravenous administration is intravenous drip infusion;
[10] The agent according to [1], wherein the pain is a neurogenic pain;
[11] The agent according to [10], wherein the neurogenic pain is cancer pain, postherpetic pain, diabetic pain, HIV-associated neurogenic pain, calculus-induced pain, neuralgia, orofacial pain or hyperalgesia;
[12] The agent according to [1], which is further combined with a fast-acting analgesic;
[13] The agent according to [1], which is further combined with one or more agents selected from an opioid analgesic, a nonopioid analgesic, an analgesic for neurogenic pain, a nonsteroidal antiinflammatory drug, an antidepressant, an antiepileptic, a central muscle relaxant, an antiemetic and a local anesthetic;
[14] The agent according to [1], wherein the control of the analgesic is reducing the dependency and/or the tolerance on the analgesic;
[15] A method for prevention, treatment or inhibition of symptom progression of a pain and/or for control of an analgesic comprising administration of (2R)-2-propyloctanoic acid, a salt thereof or a prodrug thereof to a mammal, in which an amount per dose is from 10 mg to 5000 mg;
[16] Use of (2R)-2-propyloctanoic acid, a salt thereof or a prodrug thereof for the manufacture of an agent for prevention, treatment or inhibition of symptom progression of a pain and/or for control of an analgesic comprising (2R)-2-propyloctanoic acid, a salt thereof or a prodrug thereof, in which an amount per dose is from 10 mg to 5000 mg;
[17] A method for prevention, treatment and/or inhibition of symptom progression of a pain comprising management of a mammal by a combination of the administration of a pharmaceutical composition comprising (2R)-2-propyloctanoic acid, a salt thereof or a prodrug thereof and one or more methods selected from nerve block, spinal stimulation therapy, nonconvulsive electrification, iontophoresis, acupuncture and moxibustion therapy, finger pressure, massage, electrical therapy, thermotherapy, phototherapy, spa therapy, high-pressure oxygen therapy, aroma therapy, bio-feedback, relaxation training, hypnotherapy, distraction therapy and psychological counseling; and so forth.

BEST MODE FOR CARRYING OUT THE INVENTION

In the present invention, (2R)-2-propyloctanoic acid is a compound represented by the formula (I):

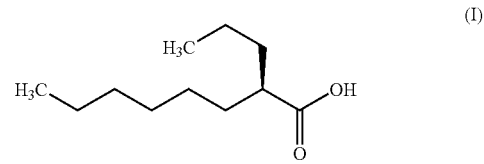

(I)

wherein ✦ represents β-configuration.

In the present invention, a preferable salt of (2R)-2-propyloctanoic acid is a pharmaceutically acceptable salt. Preferable pharmaceutically acceptable salt is a less-toxic water-soluble salt. Examples of a suitable salt of (2R)-2-propyloctanoic acid include salts with inorganic bases, salts with organic bases, salts with basic natural amino acids and so forth. Preferable examples of the salts with inorganic bases include an alkali metal salt (e.g., a sodium salt, a potassium salt, a lithium salt, etc.), an ammonium salt (e.g., a tetramethylammonium salt, a tetrabutylammonium salt, etc.) and the like. Preferable examples of the salts with organic bases include a salt with an alkylamine (e.g., methylamine, dimethylamine, trimethylamine, triethylamine, etc.), a heterocyclic amine (e.g., pyridine, picoline, piperidine, etc.), an alkanolamine (e.g., ethanolamine, diethanolamine, triethanoalnine, etc.), dicyclohexylamine, N,N'-dibenzylethylenediamine, cyclopentylamine, benzylamine, dibenzylamine, phenethylamine, tris(hydroxymethyl)methylamine, N-methyl-D-glucamine and the like. The salt with a basic natural amino acid is not particularly limited, so long as it is a salt with a basic amino acid which occurs in nature and can be purified. It is preferable to use, for example, a salt with arginine, lysine, ornithine, histidine or the like.

In the present invention, a prodrug of (2R)-2-propyloctanoic acid is not particularly limited in structure so long as it is a (2R)-2-propyloctanoic acid derivative which can be enzymatically or chemically converted into (2R)-2-propyloctanoic acid in vivo as commonly employed by those skilled in the art. Examples of the prodrug of (2R)-2-propyloctanoic acid include: [1] a compound in which a carboxyl group in (2R)-2-propyloctanoic acid has been esterified (e.g., methyl ester, ethyl ester, isopropyl ester, isobutyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester or cyclohexyloxycarbonylethyl ester of (2R)-2-propyloctanoic acid, etc.); [2] a compound in which a carboxyl group in (2R)-2-propyloctanoic acid has been amidated (e.g., methylamide, ethylamide or phenylamide of (2R)-2-propyloctanoic acid, etc.); [3] an alcohol compound in which a carboxyl group in (2R)-2-propyloctanoic acid has been reduced or a protected compound thereof (e.g., (2R)-2-propyloctanol, (2R)-2-propyloctanyl ester of acetic acid, etc.); and so forth. These compounds can be produced by publicly known methods. Also, a prodrug of (2R)-2-propyloctanoic acid may be a compound which is converted into (2R)-2-propyloctanoic acid under physiological conditions as described in *Iyakuhin no Kaihatsu*, vol. 7, *Bunshi Sekkei*, p. 163-198 (Hirokawa Shoten, 1990). Furthermore, a prodrug of (2R)-2-propyloctanoic acid may be a salt or a solvate as described above (e.g., a solvate with water, an alcoholic solvent (e.g., ethanol, etc.) or the like) which is similar to (2R)-2-propyloctanoic acid and it may be labeled with an isotope (e.g., $^3$H, $^{14}$C, $^{35}$S, $^{125}$I, etc.).

(2R)-2-propyloctanoic acid, a salt thereof or a prodrug thereof can be prepared by methods known per se, for example, the methods described in the specification of EP patent No. 0632008, WO 99/58513, WO 00/48982, the specification of JP patent No. 3032447, the specification of JP patent No. 3084345, WO 2003/051852, WO 2003/097851, WO 04/110972, methods similar thereto, or the method described in *Comprehensive Organic Transformations: A Guide to Functional Group Preparations*, 2$^{nd}$ Edition (Richard C. Larock, John Wiley & Sons Inc., 1999) or by appropriate combinations of such methods. The reaction product may be purified by conventional purification methods, for example, by distillation under atmospheric or reduced pressure, high performance liquid chromatography, thin layer chromatography or column chromatography using silica gel or magnesium silicate, or by methods such as washing and recrystallization. Also, if necessary, the product may be subjected to additional treatments such as freeze-drying.

(2R)-2-propyloctanoic acid, a salt thereof or a prodrug thereof to be used in the present invention is not limited to those which are substantially pure single substances, and they may contain impurities (e.g., byproducts, solvents, starting materials, etc. originating form the preparation process, or decomposition products, etc.) within the scope acceptable as a medicinal bulk. The content of impurities acceptable as the medicinal bulk varies depending on whether the (2R)-2-propyloctanoic acid is used, a salt thereof is used or a prodrug thereof is used, and also varies depending on the contained impurities. In the case of (2R)-2-propyloctanoic acid, for example, it is desirable that heavy metals are about 20 ppm or less, the S-form as its optical isomer is about 1.49% by mass or less, 2-propanol and heptane as the residual solvents are about 5000 ppm or less in total, and the moisture is about 0.2% by mass or less. Particularly, (2R)-2-propyloctanoic acid having an optical purity of about 99% e.e. or more, more particularly, (2R)-2-propyloctanoic acid having an optical purity of about 99.3% e.e. or more, is suitable as the (2R)-2-propyloctanoic acid to be used in the present invention.

For prevention, treatment or inhibition of symptom progression of a pain and/or for control of an analgesic, the present invention discloses a method of administering to a mammal (e.g., a human being, a nonhuman animal, etc., a human being is preferable and a patient is particularly preferable) the above-described (2R)-2-propyloctanoic acid, a salt thereof or a prodrug thereof in an effective amount, which is an amount per dose of preferably from about 1 mg to about 5000 mg, more preferably from about 10 mg to about to 5000 mg. In the method, it is particularly preferable to use a free compound, namely, (2R)-2-propyloctanoic acid. In the case of using a salt or a prodrug of (2R)-2-propyloctanoic acid, it may be used either in an amount of from about 1 mg to about 5000 mg per dose (preferably from about 10 mg to about 5000 mg per dose) as the salt or prodrug of (2R)-2-propyloctanoic acid or in an amount of from about 1 mg to about 5000 mg per dose (preferably from about 10 mg to about 5000 mg per dose) in terms of (2R)-2-propyloctanoic acid. However, the amount is preferably from about 1 mg to about 5000 mg per dose (preferably from about 10 mg to about 5000 mg per dose) in terms of (2R)-2-propyloctanoic acid. In the present invention, the term "prevention" means to prevent the onset of a pain or to decrease the pain level if any. The term "treatment" means to relieve a pain. The term "inhibition of symptom progression" means to cease or suppress the progression of a pain (e.g., enlargement of a painful area, increase in pain level, increase in pain frequency, etc.). Moreover, the term "prevention" includes the meaning of suppressing the onset of the subsequent pain in periodical pain and the meaning of preventing lowering in pain threshold, while the term "treatment" includes the meaning of restoring once lowered pain threshold. The effect that is generally called "pain relief" also falls within the scopes of "prevention" and "treatment" as used in the present invention.

The term "control of an analgesia" as used in the present invention means to exert some effect that is favorable for the living body on a matter relating to the use of an analgesic. For example, it means to reduce the amount of an analgesic used, to relieve a side effect of an analgesic, to retard the starting point of using an analgesic, to suppress the occurrence of dependency or tolerance per se caused by using an analgesic, or to decrease the extent thereof.

In the present invention, a pain may be any one so long as it is generally perceived as a pain. For example, it may be either a disease wherein a pain per se serves as the main factor of the disease as in trigeminal neuralgia or one of the symptoms of a so-called painful disease showing pain as one of the symptoms thereof such as rheumatoid arthritis. The present invention is applicable as a method for prevention, treatment and/or inhibition of symptom progression of any of these pains.

In general, pain is classified into various categories depending on characteristics. Depending on the cause of pain, for example, it is classified into, e.g., nociceptive pain, neurogenic pain, psychogenic pain and so forth. Depending on the location of pain onset, it is classified into, e.g., visceral pain, somatic pain (e.g., superficial pain, deep pain, orofacial pain, etc.), referred pain and so forth. Depending on the type of pain, moreover, it is classified into, e.g., fast pain, slow pain, acute pain, chronic pain, spontaneous pain, evoked pain, continuous pain, breakthrough pain, etc. Depending on whether or not sympathetic nerve participates, it is classified into, e.g., sympathetic independent pain, sympathetic dependent pain, etc. Furthermore, pain is sometimes classified into, e.g., cancer pain, postherpetic pain, diabetic pain, etc. depending on the disease causative of pain. In the present invention, pain may fall into any category in these classification manners. In the present invention, moreover, pain includes sensation perceived as "numbness". Namely, the pain in the present invention may be an arbitrary one perceived as "pain" or "numbness" by a mammal (e.g., a human being, a nonhuman animal, etc., a human being is preferable and a patient is particularly preferable) to whom (2R)-2-propyloctanoic acid, a salt thereof or a prodrug thereof can be administered.

Nociceptive pain may be a pain which is caused by an injury in an organ or some external stimulus with a risk of injuring an organ. Nociceptive pain, which is a pain mediated by nociceptors, can be classified into pain caused by an external stimulus (e.g., a nociceptive mechanical stimulus, a heat stimulus, a chemical stimulus, etc.) and a pain caused by an endogenous stimulus (e.g., a pain caused by an organic disease and an inflammatory pain) and so forth. More particularly, the nociceptive pain in the present invention includes pains caused by injuries on vital tissues such as an incised wound, a bruise, a bone fracture, a crush wound, a burn injury, a surgical operation, cancer and so forth.

Although psychogenic pain means a pain which occurs in association with a psychological injury, this term is used in the present invention in the meaning including a pain that cannot be explained anatomically and a pain does not associated with any lesion reflecting the pain even in the absence of any definite psychological disorder. Psychogenic pain is sometimes called chronic pain syndrome. Psychogenic pain includes, e.g., pain disorder, somatoform pain disorder, psychophysiologic disorder, psychogenic pain disorder, and so forth.

Neurogenic pain means a pathologic pain caused by dysfunction in the peripheral nerve or the central nerve system per se (brain, spinal cord, etc.) and/or a pain caused by an abnormal excitation in the pain transmission pathway which is not mediated by nociceptors. As proposed in International Association for the Study of Pain in 1994, it includes "pain caused by a transitory dysfunction in the nervous system" and a so-called neuropathic pain which is "pathological pain caused by an injury or dysfunction in the peripheral nerve and/or central nerve (central pain)". The neuropathy may be either mononeuropathy or polyneuropathy. More specifically, it means a continuous abnormal pain sensation state caused by, e.g., a lowering in pain threshold due to some dysfunction induced by a neuropathy which is evoked by an injury Or lesion in peripheral nerve, a nerve plexus or a perineural soft tissue caused by a wound, compression, infection, cancer, ischemia, a metabolic error (for example, diabetes), and so forth.

Concerning the pain in the present invention, specific disease names will be now presented. As discussed above, some of these disease names indicate pain per se while others indicate painful diseases. Also as discussed above, pain is classified into categories in accordance with several classification methods. In the following description, therefore, a single disease name is cited repeatedly in several categories.

Examples of the pain in the present invention include headache (e.g., migraine, tension-type headache, cluster headache, other symptomatic headache, etc.), orofacial pain (e.g., toothache, glossodynia, temporomandibular joint disorders, trigeminal neuralgia, etc.), neck-shoulder-arm pain (e.g., cervical disc herniation, cervical osteochondrosis, shoulder-arm-neck syndrome, periarthritis humeroscapularis (frozen shoulder), cervical spinal canal stenosis, thoracic outlet syndrome, traumatic brachial plexus injury, shoulder-hand syndrome, post-traumatic cervical syndrome (whiplash injury), etc.), breast pain, abdominal pain (e.g. acute abdomen, cholelitiasis, acute pancreatitis, urolithiasis, etc.), low back pain (e.g., lumbar disc herniation, lumbar spondylosis deformans, lumbar spinal canal stenosis, lumber spondylolysis, lumbar facet syndrome, pondylolisthesis, etc.), knee pain, musculoskeletal pain [e.g., myalgia (e.g., myofascial pain syndrome (MPS), fibromyalgia syndrome (EMS), etc.), arthalgia (e.g., arthritis, rheumatatoid arthritis (RA), gout, etc.), vertebral pain, bone pain, etc.], blood flow-related pain (e.g., arteriosclerosis obliterans (ASO), Buerger's disease (thromboangiitis obliterans (TAO), etc.), traumatic pain, neurogenic pain [e.g., neuralgia (e.g., trigeminal neuralgia, intercostal neuralgia, parethesic femoral neuralgia, inguinal neuralgia, saphenous neuralgia, median neuralgia, ulnar neuralgia, sciatica, radicular pain, etc.), herpetic pain (e.g., acute herpetic pain, postherpetic pain (chronic stage), etc.), diabetic pain (e.g., diabetic neuropathy, large fiber neuropathy, small fiber neuropathy, proximal motor neuropathy, acute mononeuritis, compression paralysis, etc.), entrapment syndrome (e.g., thoracic outlet syndrome, suprascapular entrapment neuropathy, scapular dorsal entrapment neuropathy, quadrilateral space syndrome, round pronator muscle syndrome, anterior interosseous syndrome, cubital tunnel syndrome, tardy ulnar nerve palsy, posterior interosseous syndrome, carpal tunnel syndrome, ulnar tunnel syndrome, Wartenberg's disease, Blowler's thumb, parethesic femoral neuralgia, piriformis syndrome, Hunter tunnel syndrome, common peroneal nerve entrapment neuropathy, tarsal tunnel syndrome, anterior tarsal tunnel syndrome, Morton's disease, cervical spinal canal stenosis, lumbar spinal canal stenosis, diffuse spinal canal stenosis, etc.), lumber pain-related neuropathy, traumatic brachial plexus injury, reflex sympathetic dystrophy (complicated local pain syndrome type 1), reflex sympathetic atrophy, causalgia (burning pain, complicated local pain syndrome type 2), painful neuropathy, pain after spinal cord injury, phantom pain (e.g., phantom limb pain, phantom tooth pain, etc.), central pain (e.g., thalamic syndrome, Dejerine-Roussy syndrome, thalamic pain (e.g., post stroke thalmic pain), post stroke pain, etc.), deafferentation pain, iatrogenic neuropathy, sympathetic maintained pain, angry backffiring C-nociceptor syndrome (ABC syndrome), cancer pain, HIV-associated neurogenic pain, calculus-induced pain (e.g., pain induced by urethral calculus (e.g., renal calculus, urinary tract calculus, bladder calculus, urethral calculus, etc.), pain induced by gallbladder calculus, pain induced by deferential calculus, etc.), postoperative pain, chronic headache, orofacial pain (e.g., toothache, glossodynia, temporomandibular joint disorders, trigeminal neuralgia, etc.), atypical orofacial pain (e.g., atypical facial pain after tooth removal, etc.), periarthritis humeroscapularis, arthrosis deformans, arthritis, pain associated with rheumatism, back pain, multiple sclerosis, pain induced by drug therapy, pain induced by radiotherapy, pain caused by an insufficient narcotic analgesic effect, etc.].

The pain suitable in the present invention is a neurogenic pain (in particular, cancer pain, postherpetic pain, diabetic pain, HIV-associated neurogenic pain, calculus-induced pain, neuralgia, orofacial pain, etc.). In addition to the diseases as described above, hypersthesia (in particular, hyperalgesia, spontaneous pain and so forth are also suitable as the neurogenic pain in the present invention.

Depending on the purpose, "an agent for prevention, treatment or inhibition of symptom progression of a pain and/or for control of an analgesic which contains (2R)-2-propyloctanoic acid, a salt thereof or a prodrug thereof" according to the present invention (hereinafter sometimes abbreviated as "the agent of the present invention") can be roughly classified into "an agent for prevention, treatment or inhibition of symptom progression of a pain comprising (2R)-2-propyloctanoic acid, a salt thereof or a prodrug thereof" and "an agent for control of an analgesic comprising (2R)-2-propyloctanoic acid, a salt thereof or a prodrug thereof". As the pain that is the subject of "an agent for prevention, treatment or inhibition of symptom progression of a pain comprising (2R)-2-propyloctanoic acid, a salt thereof or a prodrug thereof", a neurogenic pain is suitable from among the pains which are cited above. In particular, cancer pain, postherpetic pain, diabetic pain, HIV-associated neurogenic pain, calculus-induced pain, neuralgia, orofacial pain, hyperalgesia and so forth are suitable therefor. This "agent for prevention, treatment or inhibition of symptom progression of a pain comprising (2R)-2-propyloctanoic acid, a salt thereof or a prodrug thereof" can be used for prevention, treatment or inhibition of symptom progression of these pains, in particular, a pain caused by allodynia.

On the other hand, "an agent for control of an analgesic comprising (2R)-2-propyloctanoic acid, a salt thereof or a prodrug thereof" makes it possible to reduce the amount of an analgesic used, to relieve a side effect of an analgesic, to retard the starting point of using an analgesic, to suppress the occurrence of dependency or tolerance per se caused by using an analgesic, or to decrease the extent thereof, as described above. The "analgesic" as described herein may be any agent having an effect of relieving a pain. As it will be discussed hereinafter, examples thereof include an opioid analgesic, an analgesic for neurogenic pain, a nonopioid analgesic, a nonsteroidal antiinflammatory drug, an analgesic adjuvant, an antidepressant, an antiepileptic, a central muscle relaxant, a local anesthetic and so forth. Among them, one falling within the category of fast-acting analgesics which will be described hereinafter is preferable. An opioid analgesic or a nonsteroidal antiinflammatory drug is more preferable and an opioid analgesic is still preferable. Specific effects that can be achieved by using "an agent for control of an analgesic comprising (2R)-2-propyloctanoic acid, a salt thereof or a prodrug thereof" includer for example, ameliorating digestive disorders induced by a nonsteroidal antiinflammatory agent, ameliorating constipation or diarrhea induced by an opioid analgesic, reducing the dose of a fast-acting analgesic, suppressing the occurrence of dependency or tolerance per se caused by using an opioid analgesic or to decreasing the extent thereof and so forth. By achieving the above-described effects with the use of "an agent for control of an analgesic comprising (2R)-2-propyloctanoic acid, a salt thereof or a prodrug thereof", it becomes possible to achieve additional favorable effects that, e.g., the analgesic can be used for a long time.

For prevention, treatment or inhibition of symptom progression of a pain, or for control of an analgesic (preferably for the reduction of the dependency and/or tolerance of an analgesic), feature of the agent of the present invention is that (2R)-2-propyloctanoic acid, a salt thereof or a prodrug thereof is administered in an amount per dose of about 1 mg to about 5000 mg, preferably in an amount per dose of from about 10 mg to about 5000 mg. The (2R)-2-propyloctanoic acid, a salt thereof or a prodrug thereof may be administered either orally or parenterally. The parenteral administration may be either systemic administration such as intravenous administration or topical administration such as intrathecal administration or transdermal administration. By altering the administration method, an administration dose required for achieving a desirable effect also alters. In the case of orally administering (2R)-2-propyloctanoic acid, a salt thereof or a prodrug thereof, for example, the amount per dose of the (2R)-2-propyloctanoic acid, a salt thereof or a prodrug thereof is preferably from about 100 mg to about 5000 mg, more preferably from about 100 mg to about 1800 mg and particularly preferably from about 300 mg to about 1200 mg. In the case of intravenously administering (2R)-2-propyloctanoic acid, a salt thereof or a prodrug thereof, for example, the amount per dose of the (2R)-2-propyloctanoic acid, a salt thereof or a prodrug thereof is preferably from about 100 mg to about 2000 mg, more preferably from about 300 mg to about 1200 mg. In the case of intrathecally administering (2R)-2-propyloctanoic acid, a salt thereof or a prodrug thereof, for example, the amount per dose of the (2R)-2-propyloctanoic acid, a salt thereof or a prodrug thereof is preferably from about 1 mg to about 1000 mg, more preferably from about 1 mg to about 500 mg and particularly preferably from about 10 mg to about 500 mg. In the case of transdermally administering (2R)-2-propyloctanoic acid, a salt thereof or a prodrug thereof, for example, the amount per dose of the (2R)-2-propyloctanoic acid, a salt thereof or a prodrug thereof is preferably from about 1 mg to about 500 mg, more preferably from about 1 mg to about 50 mg.

In the case of intravenously administering (2R)-2-propyloctanoic acid, a salt thereof or a prodrug thereof in order to obtain preferable effects of preventing, treating or inhibiting symptom progression a pain as described above or to obtain an effect of controlling an analgesic, the dose thereof can be specified depending on the body weight of a mammal (e.g., a human being, a nonhuman animal, etc., preferably a human being and particularly preferably a patient). In the case of a patient, it is preferable to administer, for example, from about 1 mg to about 20 mg, more preferably from about 2 mg to about 18 mg, thereof per 1 kg of the body weight of the patient. As a more preferable dose, for example, it can be about 2 mg, about 4 rag, about 6 mg, about 8 mg, about 10 mg, about 12 mg, about 15 mg, about 18 mg and so forth per 1 kg of the body weight of the patient. As a more preferable dose, for example, it can be about 4 mg, about 6 mg, about 8 mg, about 10 mg, about 12 mg and so forth per 1 kg of the body weight of the patient. As the most preferable dose, for example, it can be about 8 mg, about 10 mg and so forth per 1 kg of the body weight of the patient. In the case of specifying the dose depending on body weight as stated above, it is also preferable even that the total amount per dose is excluded from the preferable range in intravenous administration as described above (about 100 mg to about 2000 mg).

In the case of intravenously administering (2R)-2-propyloctanoic acid, a salt thereof or a prodrug thereof, a side effect caused by a rapid increase in the concentration thereof in the blood can be prevented or, if desired, the concentration thereof in the blood can be controlled by continuously administering (preferably intravenous drip infusion) it into the vein with the use of, for example, an injection cylinder, an infusion bag, etc. The continuous administration period is not particularly restricted but may be altered depending on the conditions of a mammal (e.g., a human being, a nonhuman animal, etc., preferably a human being and particularly preferably a patient) or other factors. For example, it is preferred to conduct a single continuous administration over about 0.5 hour to about 3 hours. It is preferable about 0.5 hour to about 1.5 hours and particularly preferable for about 1 hour.

To administer (2R)-2-propyloctanoic acid, a salt thereof or a prodrug thereof to a mammal (e.g., a human being, a nonhuman animal, etc., human being is preferable and a patient is particularly preferable) by using the administration method as described above, a medicinal composition which is appropriate for each administration method is used.

For example, a medicinal composition to be used in the injection administration (e.g., intravenous administration, intrathecal administration, etc.) such as a so-called infusion preparation, an injection, etc. can be prepared by dissolving (2R)-2-propyloctanoic acid, a salt thereof or a prodrug thereof together with a metal salt commonly used in injections (e.g., trisodium phosphate, disodium monohydrogen phosphate, sodium carbonate, sodium sulfite, etc.), a pH controlling agent (e.g., sodium hydroxide, etc.) as well as additives reported in, for example, *Iyakuhin Tenkabutsu Jiten*, ed. by Nippon lyakuhin Tenkazai Kyokai, Yakuji Nipposha (2000), etc. such as a stabilizer, a surfactant, a buffering agent, a solubilizer, an antioxidant, a defoaming agent, an isotonic agent, an emulsifier, a suspending agent, a preservative, a soothing agent, a dissolving agent, a dissolving aid and the like in a solvent (e.g., distilled water for injection, etc.). In the case of an infusion preparation, the components which is generally used in infusions such as an electrolyte (e.g., sodium chloride, potassium chloride, calcium chloride, sodium lactate, sodium dihydrogen phosphate, sodium carbonate, magnesium carbonate, etc.), a sugar (e.g., glucose, fructose, sorbitol, mannitol, dextran, etc.), a proteinous amino acid (e.g., glycine, aspartic acid, lysine, etc.), a vitamin (e.g., vitamin $B_1$, vitamin C, etc.) and the like can be used, in addition to the additives as cited above. Such a medicinal composition is sterilized in the final step or produced or prepared by an aseptic operation method. It is also possible that an aseptic solid agent such as a freeze-dried product is produced and dissolved in sterilized or aseptic purified water or another solvent before using.

A composition to be used in oral administration, i.e., a so-called oral preparation may be in any dosage form so long as it can be orally administered to a mammal (e.g., a human being, a nonhuman animal, etc., preferably a human being and particularly preferably a patient). It is preferable that an oral preparation comprising (2R)-2-propyloctanoic acid, a salt thereof or a prodrug thereof to be used in the present invention is, for example, a tablet, a capsule, subtle granules, granules, a powder, etc. A capsule is preferable and a soft capsule is particularly preferable. For example, a preparation such as a tablet, subtle granules, granules, a powder, etc. can be produced by using (2R)-2-propyloctanoic acid, a salt thereof or a prodrug thereof together with a filler, a binder, a disintegrating agent, a lubricant and the like which are commonly used. Examples of the filler include sucrose, lactose, glucose, starch, mannitol, sorbitol, cellulose, talc, cyclodextrin, and the like. Examples of the binder include cellulose, methylcellulose, polyvinylpyrrolidone, gelatin, gum arabic, polyethylene glycol, sucrose, starch, and the like. Examples of the disintegrating agent include starch, carboxymethylcellulose, carboxymethylcellulose calcium salt, and the like. Examples of the lubricant include talc, and the like. A soft capsule can be produced by, for example, coating (2R)-2-propyloctanoic acid, a salt thereof or a prodrug thereof with a capsule coating commonly used. A capsule coating can be produced by using a capsule base and a plasticizer as the essential components optionally together with, if required, a flavoring agent, a preservative, a coloring gent, an opacifying agent, a solubility-controlling agent, and the like. Examples of the capsule base include a protein ((e.g., gelatin, collagen, etc.), a polysaccharide (e.g., starch, amylose, polygalacturonic acid, agar, carrageenan, gum arabic, gellan gum, xanthan gum, pectin, alginic acid, etc.), a biodegradable plastic (e.g., polylactic acid, polyhydroxybutyric acid, polyglutamic acid, etc.), a hardened fat (e.g., triglyceride or diglyceride of medium chain fatty acids, etc.), and the like. As the plasticizer, it is possible to use a sugar, a sugar alcohol, a polyhydric alcohol, and the like and examples thereof include glycerol, sorbitol, polyethylene glycol, and the like. Examples of the flavoring agent include peppermint oil, cinnamon oil, essence or flavor of a fruit such as strawberry, and the like. Examples of the preservative include ethyl parahydroxybenzoate, propyl parahydroxybenzoate, and the like. Examples of the coloring agent include Yellow No. 4, Yellow No. 5, Red No. 3, Blue No. 1, copper chlorofine, and the like. Examples of the opacifying agent include titanium dioxide, red iron oxide, and the like. Examples of the solubility-controlling agent include cellulose acetate phthalate, an alkali metal salt of hydroxypropylmethylcellulose, an alkali metal salt of hydroxymethylcellulose acetate succinate, an alkali alginate, an alkali metal polyacrylate, methylcellulose, carboxymethylcellulose, casein, collagen, agar powder, polyvinyl alcohol, pectin, and the like.

A composition to be used in transdermal administration, i.e., a so-called transdermal preparation may be in any dosage form so long as it can be transdermally administered to a mammal (e.g., a human being, a nonhuman animal, etc., preferably a human being is preferable and a patient is particularly preferable). Examples of the transdermal preparation to be used in the present invention include a liquid spray, a lotion, an ointment, a cream, a gel, a sol, an aerosol, a patch, a plaster, a tape, and the like. In these compositions, (2R)-2-propyloctanoic acid, a salt thereof or a prodrug thereof is used together with an oily base or a water-soluble base which are commonly used in external preparations, a pressure-sensitive adhesive used in tapes, a film base, a gel base, an emulsion base prepared by adding a surfactant to an oily base or a water-soluble base and the like. If necessary, it is also possible to add a surfactant (e.g., an anionic surfactant (e.g., a fatty acid, saponin, a fatty acid sarcoside, an alcohol sulfate ester, an alcohol phosphate ester, etc.), a cationic surfactant (e.g., a quaternary ammonium salt, a heterocyclic amine, etc.), an amphoteric surfactant (e.g., an alkyl betaine, lysolecithin, etc.), a nonionic surfactant (e.g., a polyoxyethylene alkyl ether, a polyoxyethylene sorbitan fatty acid ester, a sucrose fatty acid ester, etc.) etc.), a thickener (e.g., a cellulose derivative (e.g., carboxymethylcellulose, etc.), a polycarboxylic acid (e.g., polyacrylic acid, methoxymethylene-maleic anhydride copolymer, etc.), a nonionic water-soluble polymer (e.g., polyvinylpyrrolidone, polyvinyl alcohol, etc.) etc.), a stabilizer (e.g., an antioxidant (e.g., ascorbic acid, sodium pyrosulfite, etc.), a chelating agent (e.g., EDTA, etc.), a pH-adjusting agent (e.g., a phosphate buffer, sodium hydroxide, etc.), a preservative (e.g., a paraben, an alkyl quaternary ammonium salt (e.g., benzalkonium chloride, benzetonium chloride, etc.), an absorption promoting aid (e.g., a fatty acid and its ester (e.g., oleic acid, isopropyl myristate, etc.), a phospholipid (e.g., phosphatidylcholine, etc.), a terpene (e.g., limonene, etc.), an azacycloalkane (e.g., Azone (trade name, Nelson Research), etc.) and the like. Examples of the oily base include a vegetable oil (e.g., cottonseed oil, sesame oil, olive oil, etc.), a wax (e.g., carnauba wax, bees wax, etc.), a higher hydrocarbon (e.g., white vaseline, liquid paraffin, plastibase, etc.), a fatty acid (e.g., stearic acid, palmitic acid, etc.) and its ester, a higher alcohol (e.g., cetanol, etc.), a silicone compound (e.g., silicone fluid, silicone rubber, etc.) and the like. Examples of the water-soluble base include polyvinyl alcohol, carboxyvinyl polymer, a solution or a high-molecule hydrogel of a cellulose derivative and the like, polyethylene glycol (official preparation: macrogol), polyethylene glycol-polypropylene glycol copolymer, propylene glycol, 1,3-butylene glycol, ethanol, glycerol, and the like. Examples of the pressure-sensitive adhesive to be used in tapes include a synthetic rubber-based pressure-sensitive adhesive (e.g., methacrylic acid ester copolymer, a natural rubber-based pressure-sensitive adhesive, synthetic isoprene, etc.), a silicone polymer-based pressure-sensitive adhesive and the like. Examples of the film base include polyethylene, polypropylene, polyethylene-vinyl acetate copolymer, PET, an aluminum laminate and the like. Examples of the gel base include dry agar, gelatin, aluminum hydroxide, silicic acid, and the like. Examples of the surfactant to be used in an emulsion base include an anionic surfactant (e.g., a fatty acid, saponin, a fatty acid sarcoside, an alcohol sulfate ester, an alcohol phosphate ester, etc.), a cationic surfactant (e.g., a quaternary ammonium salt, a heterocyclic amine, etc.), an amphoteric surfactant (e.g., an alkyl betaine, lysolecithin, etc.), a nonionic surfactant (e.g., a polyoxyethylene alkyl ether, a polyoxyethylene sorbitan fatty acid ester, a sucrose fatty acid ester, etc.) and so forth. A preparation for transdermal administration comprising (2R)-2-propyloctanoic acid, a salt thereof or a prodrug thereof is prepared by a conventional method with the use of various bases or a pressure-sensitive adhesive as described above optionally together with other additive(s), if necessary.

For example, a liquid spray, a lotion, a sol or an aerosol can be produced by dissolving or dispersing (2R)-2-propyloctanoic acid, a salt thereof or a prodrug thereof in a solvent such as water, propylene glycol, 1,3-butylene glycol, ethanol, glycerol or the like. If necessary, additive(s) as described above may be added.

An ointment or a cream can be produced by mixing (2R)-2-propyloctanoic acid, a salt thereof or a prodrug thereof with the above-described water-soluble base, the above-described oily base and/or water and a solvent which is commonly employed in the art such as a vegetable oil, adding a surfactant if necessary, and then emulsifying. If necessary, additive(s) as described above may be added.

A patch, a plaster or a tape can be produced by applying a solution comprising (2R)-2-propyloctanoic acid, a salt thereof or a prodrug thereof and the above-described pressure-sensitive adhesive (optionally containing the above-described additive(s) it necessary) on the film base as described above followed by, if necessary, crosslinking or drying.

A gel can be produced by pouring a solution comprising (2R)-2-propyloctanoic acid, a salt thereof or a prodrug thereof and the above-described gel base (optionally containing the above-described additive(s) if necessary) into a mold followed by, if necessary, crosslinking or drying.

In the case of applying such a medicinal composition to prevention, treatment and/ox inhibition of symptom progression of a pain, in particular, a neurogenic pain or the like, the administration of the medicinal composition can be any of the periods, for example, until the onset of the disease is substantially inhibited in the case of desiring a preventive effect; until the treatment is substantially completed in the case of desiring a treatment effect; or until the progression of the symptom is substantially inhibited in the case of desiring an effect of inhibiting symptom progression. If necessary, it can be administered intermittently with an appropriate drug holiday. In the intermittent administration, it is preferable that the drug holiday is 1 day or longer but not longer than 30 days. For example, it may be intermittent administration of every second day, intermittent administration consisting of two administration days and one cession day, intermittent administration consisting of five continuous administration days and two cession days, or intermittent administration of the so-called calender system (namely in the case of tablets, being called "calender tablets"). In intrathecal administration, for example, it is administered almost twice or thrice per day.

In the case of applying such a medicinal composition to control of an analgesic, the administration of the medicinal composition can be any of the periods until the desiring effect can be substantially established. As a matter of course, it can be intermittently administered as described above.

For example, the dosing period of the agent of the present invention in the case of, for example, oral administration or transdermal administration is from 1 day to 5 years and the like, preferably from 1 day to 1 year and the like, more preferably from 1 day to 6 months and the like, and particularly preferably from 1 day to 2 months and the like. In the case of intravenous administration, the dosing period is from 1 day to 100 days and the like, preferably from 1 day to 10 days and the like, more preferably from 1 day to 7 days and the like, and most preferably for 7 days and the like. In the case of intrathecal administration, the dosing period is from 1 day to 3 years and the like, preferably from 1 day to 1 year and the like, more preferably from 1 day to 6 months and the like, and most preferably from 1 day to 3 months and the like.

During the dosing period in oral or intravenous administration, the dosing time per day is, for example, 1 to 5 times and the like, preferably 1 to 3 times and the like, more preferably 1 to 2 times and the like and most preferably 1 time and the like. In intrathecal administration, although it may be administered 1 to 2 times and the like per day, intermittent administration as described above is more preferable. Since a topical effect can be expected in transdermal administration, when it is administered to an affected site on the perception of a pain, an improved effect can be obtained.

In the present invention, (2R)-2-propyloctanoic acid, a salt thereof or a prodrug thereof may be used either alone or as a combination with other agents or treatment methods which have been used in treating a pain.

In the case of the use in combination with another agent, it is possible to administer a preparation containing both components. Alternatively, the individual preparations may be separately administered. The administration as separate preparations may be either simultaneous administration or time-lag administration. Examples of the agent to be used together include an opioid analgesic (e.g., morphine, codeine, fentanyl, meperidine, methadone, propoxyphene, levorphanol, hydromorphone, oxycodone, oxymorphone, pentazocine, etc.), and an analgesic for neurogenic pain (e.g., ziconotide, ABSU17, AC-262271, ACP-102, ADX-1, AV-333, AZD-6538, CGP-35024, CPI-1714, DP-236, EN-3215, galantamine, JO-1614, M-58996, Neublastin, RWJ38116, VX-409, YT-1006, fentanyl patch, levetiracetam, memantine, tiagabine, zonisamide, ABT-894, AZD-4282, Lamictal XR, M-40403, T-62, becampanel, CNP-3381, CNS-5161, KDS-2000, ketamine+amitriptyline combination cream, radafaxine, ralfinamide, REN-1654, ReN-1869, traxoprodil, valrocemide, a botulinus toxin preparation (e.g., Dysport, etc.), lacosamide, NGX-4010, Tectin, AVP-923, rufinamide, GW-1000, etc.), an antiemetic (e.g., metoclopramide, hydroxyzine, prochlorperazine, etc.), a nonopioid analgesic (e.g. nonsteroidal antiinflammatory drugs (NSAIDs) (e.g., aspirin, ibuprofen, ketoprofen, loxoprofen, naproxen, acetaminophen, celecoxib, rofecoxib, valdecoxib, etc.), etc.), an analgesic adjuvant (e.g., an antidepressant (e.g., amitriptyline, desipramine, etc.), an antiepileptic (e.g., a gabapentinoid (e.g., gabapentin, pregabalin, etc.), carbamazepine, phenytoin, clonazepam, divalproex, lamotrigine, topiramate, oxcarbazepine, etc.), a central muscle relaxant (e.g., baclofen, etc.), a local anesthetic (e.g., mexiletine, lidocaine, etc.) and so forth. In particular, opioid analgesics, analgesics for neurogenic pain and nonopiod analgesics such as nonsteroidal antiinflammatory agents are sometimes called fast-acting analgesics in general.

In the case of combining with another treatment method, the administration of (2R)-2-propyloctanoic acid, a salt thereof or a prodrug thereof may be conducted either simultaneously with the other treatment method or separately. Examples of another treatment method include nerve block (e.g., trigger point block, stellate ganglion block, brachial plexus block, suprascapular nerve block, epidural block, radicular block, intervertebral joint block, differential block, sciatic nerve block, intercostal nerve block, etc.), spinal stimulation therapy, nonconvulsive electrification, iontophoresis, acupuncture and moxibustion therapy (e.g., electroacupuncture, still acupuncture, moxibustion, etc.), finger pressure, massage, electrical therapy (e.g., transcutaneous electrical nerve stimulation (TENS), low-frequency therapy, etc.) thermotherapy (e.g., hot pack, cryotherapy, diathermy, ultra-high frequency wave therapy, etc.), phototherapy (e.g., low power laser, polarized near infrared therapy, etc.), spa (water) therapy (e.g., hot spring cure, hot spring drinking, mineral clay bath, aquatic functional training, etc.), high-pressure oxygen therapy, aroma therapy, bio-feedback and other cognitive techniques (e.g., relaxation training, hypnotherapy, distraction therapy, etc.), psychological counseling and so forth.

The above-described agents which are used in combination with a pharmaceutical composition comprising (2R)-2-propyloctanoic acid, a salt thereof or a prodrug thereof are only examples and are not limited thereto. These agents to be used combinedly may be administered by any way without particular restriction, namely, either orally or parenterally. Also, these agents may be administered in any combination of two or more. Furthermore, the agents for combination use include those which have been found as well as those which will be found, based on the mechanism described above.

[Toxicity]

Since the toxicity of (2R)-2-propyloctanoic acid, a salt thereof or a prodrug thereof is extremely low, it can be considered to be sufficiently safe for medicinal uses. For example, in a single intravenous administration test in which (2R)-2-propyloctanoic acid was administered in a dose of 100 mg/kg to dogs, no fatal case was observed.

[Application to Medicament]

The present invention comprises administering (2R)-2-propyloctanoic acid or a salt or prodrug thereof for preventing, treating and/or inhibiting symptom progression of a pain or for controlling an analgesic, an effective amount, wherein amount per dose is from 1 mg to 5000 mg and more preferably an amount per dose of from 10 mg to 5000 mg of (2R)-2-propyloctanoic acid, a salt thereof ox a prodrug thereof is administered. A pharmaceutical composition comprising (2R)-2-propyloctanoic acid or a salt or prodrug thereof to be used in the present invention comprises (2R)-2-propyloctanoic acid or a salt or prodrug thereof as the active ingredient, and can be used for achieving the above-described object in a mammal (e.g., human being, a non-human animal such as monkey, sheep, bovine, horse, dog, cat, rabbit, rat, mouse, etc.). Particularly, by systematically administering via an oral or parenteral route by a preferable method with a preferable dose as disclosed by the present invention to a mammal (e.g., human being, a non-human animal, preferably a human being and more preferably a patient), or by topically administering by, for example, intrathecal administration or transdermal administration, preferable effects of, for example, preventing, treating and/or inhibiting symptom progression of a pain, in particular, a neurogenic pain, suppressing the dependency on an analgesic (in particular, an opioid analgesic) or tolerance thereto, reducing the amount of an analgesic used, retarding the starting point of using the same or relieving a side effect thereof can be obtained.

According to the present invention, it is possible to provide specific administration methods aiming at using (2R)-2-propyloctanoic acid, a salt thereof or a prodrug thereof for a pain. By administering (2R)-2-propyloctanoic acid, a salt thereof or a prodrug thereof by a preferable method with a preferable dose as disclosed by the present invention, it is possible to achieve the effects of preventing, treating and/or inhibiting symptom progression of a pain or the effects of controlling an analgesic as described above. For example, a desirable effect on a pain, in particular, an analgesic effect can be exerted as will be shown in the following Examples. Accordingly, the present invention can provide a treatment method which is effective for a patient suffering from a pain that cannot be ameliorated by the existing treatment methods, for example, the symptom of allodynia.

EXAMPLES

Although the present invention will be described in detail by referring to the following Examples, the present invention is not limited thereto.

It has been demonstrated by, for example, the following experiments that (2R)-2-propyloctanoic acid or a salt or prodrug thereof has an effect of relieving a pain (an analgesic effect). Measurement methods for evaluating (2R)-2-propyloctanoic acid or a salt or prodrug thereof were modified as follows so as to improve the measurement accuracy and/or measurement sensitivity. Detailed experiment methods are shown as follows.

Example 1

Evaluation of the Efficacy of (2R)-2-Propyloctanoic Acid in Rat Spinal Nerve Ligation Model (1) Making of Spinal Nerve Ligation Model Rat Male rats were used in the experiment. Spinal nerve ligation models were made in accordance with the method of Kim & Chung (Kim, S. H. & Chung, J. M., *An experimental model for peripheral neuropathy produced by segmental spinal nerve ligation in the rat*, Pain, 50, 355-363, 1992). Namely, the fifth lumber nerve in one side was strongly ligated with silken threads.

More specifically, the models were made in the following manner.

After intraperitoneally administering 40 mg/kg (liquid volume 0.8 ml/kg) of pentobarbital (Nenbutal Injection (trade name), Dainippon Pharmaceutical Co., Ltd.), a rat was fixed in the dorsal position under anesthesia and the abdomen was incised in the median line with scissors. The intestines and the like were pushed aside with sterilized gauze and the abdominal aorta and the abdominal vein were confirmed. Then, the muscle located immediately below the iliolumbar vein was cleaved with tweezers. After confirming the fourth lumber nerve and the fifth lumber nerve in the muscle, the fifth lumber nerve (L5) was ligated with 6-0 silken threads. Subsequently, the intestines having been pushed away were returned to the original positions. 5 ml of physiological saline (otsuka Pharmaceutical Factory, Inc.) containing ampicillin sodium (Viccillin for Injection (trade name), Meiji Seika Kaisha, Ltd.) (ampicillin concentration: 20 mg/ml) was poured into the peritoneal cavity, and the abdominal muscles and skin were sutured with a nylon thread.

(2) Administration of Agents

From immediately after the spinal nerve ligation, 30 mg/kg of (2R)-2-propyloctanoic acid was orally administered once a day for 14 days (14 times in total). Also, vehicle control was administered in the same manner.

(3) Evaluation of Hyperalgesia (3-1) Measurement of Latent Time of Pain Response (Latent Time of Heat Stimulus) (Evaluation of Heat Hyperalgesia)

On the next day of the final administration, the latent time of heat stimulus was measured. Namely, right and left footpads were irradiated with infrared light of a halogen lamp from the lower side, and the time until the occurrence of an escape response (the latent time of pain reaction: sec) was measured.

(3-2) Measurement of Escape Threshold of Contact Stimulus (Evaluation of Contact Allodynia)

On the next day of the final administration, the escape threshold of a contact stimulus was measured. Namely, filaments (von Frey filaments: VFF) were pressed against right and left footpads from the lower side. Then, the VFF indication at the occurrence of an escape response was recorded and converted into weight (g).

<Results>
Measurement of Latent Time of Pain Response (Latent Time of Heat Stimulus) (Evaluation of Heat Hyperalgesia)

(2R)-2-propyloctanoic acid or a vehicle was administered to spinal nerve ligation model rats and the latent time of a pain response (the latent time of a heat stimulus) was measured to examine the effect of (2R)-2-propyloctanoic acid on heat hyperalgesia. Table 1 shows the results.

TABLE 1

| Group | Dose (mg/kg) | Number of animals | Latent time of pain response (sec) | |
|---|---|---|---|---|
| | | | Normal side | Injured side |
| Vehicle control | 0 | 20 | 19.96 ± 6.53 | 8.18 ± 3.02 |
| (2R)-2-propyloctanoic acid | 30 | 20 | 19.00 ± 5.58 | 13.61 ± 6.76 |

In the vehicle control group, the latent time of the pain response (the latent time of the heat stimulus) on the day 14 after the operation was 19-96 sec in the normal side (the opposite side) while that in the injured side (operated-on side) was lower (8.18 sec), which indicated the onset of heat hyperalgesia. In the (2R)-2-propyloctanoic acid-administered group, the latent time of the pain response (the latent time of the heat stimulus) on the day 14 after the operation was 19.00 sec in the normal side (the opposite side), which shows no difference from the vehicle control group. On the other hand, the latent time of the pain response in the injured side (operated-on side) was 13.61 sec. Namely, it is significantly higher ($p<0.01$: Welch test, compared with the vehicle control) than that in the vehicle control group (8.18 sec). Thus, an analgesic effect on heat hyperalgesia was confirmed.

Measurement of Escape Threshold of Contact Stimulus (Evaluation of Contact Allodynia)

(2R)-2-propyloctanoic acid or a vehicle was administered to spinal nerve ligation model rats and the escape threshold of a contact stimulus was measured to examine the effect of (2R)-2-propyloctanoic acid on contact allodynia. Table 2 shows the results.

TABLE 2

| Group | Dose (mg/kg) | Number of animals | Escape threshold of contact stimulus (g) | |
|---|---|---|---|---|
| | | | Normal side | Injured side |
| Vehicle control | 0 | 20 | 57.9 ± 30.7 | 2.8 ± 3.6 |
| (2R)-2-propyloctanoic acid | 30 | 20 | 66.1 ± 29.8 | 14.7 ± 12.7 |

In the vehicle control group, the latent escape threshold of the contact stimulus on the day 14 after the operation was 57.9 g in the normal side (the opposite side) while that in the injured side (operated-on side) was lower (2.8 g), which indicated the onset of allodynia against the contact stimulus (contact allodynia). In the (2R)-2-propyloctanoic acid-administered group, the escape threshold of the contact stimulus on the day 14 after the operation was 66.1 g in the normal side (the opposite side), which shows no difference from the vehicle control group. On the other hand, the escape threshold of the contact stimulus in the injured side (operated-on side) was 14.7 g, namely, which is significantly higher ($p<0.01$: Welch test, compared with the vehicle control) than that in the vehicle control group (2.8 g). Thus, an analgesic effect on contact allodynia was confirmed.

PREPARATION EXAMPLES

Preparation Example 1

Production of Injection Comprising (2R)-2-Propyloctanoic Acid

To water for injection, (2R)-2-propyloctanoic acid (2.0 kg) and trisodium phosphate 12-hydrate (3.54 kg) were added. The total amount was adjusted to 40 L with the water for injection. After obtaining a homogeneous solution, it was filtered through a sterilizing filter (Durapore 0.22 μm membrane) and packed in plastic ampules in 2 mL portions. After sterilizing with steam under elevated pressure (123° C., 15 minutes), 20,000 ampules containing 100 mg per ampule of the active ingredient were obtained.

Preparation Example 2

Production of Soft Capsules Comprising (2R)-2-Propyloctanoic Acid

Gelatin (20 kg) and conc. glycerol (6 kg) were blended together in the presence of purified water (20 kg) under 70° C. to give a homogeneous solution. The solution and (2R)-2-propyloctanoic acid (0.9 kg) were supplied into a soft capsule encapsulating machine (a rotary soft capsule molding machine Model H-1; KAMATA) to give coarse soft capsules having (2R)-2-propyloctanoic acid encapsulated therein. The coarse soft capsules subjected to tumbler drying and a tray drying successively. Thus, soft capsules (2200 capsules) comprising 300 mg of (2R)-2-propyloctanoic acid per capsule were obtained.

INDUSTRIAL APPLICABILITY

The agent of the present invention for prevention, treatment or inhibition of symptom progression of a pain and/or for control of an analgesic comprising (2R)-2-propyloctanoic acid, a salt thereof or a prodrug thereof, in particular, the agent for prevention, treatment or inhibition of symptom progression of a pain and/or for control of an analgesic comprising (2R)-2-propyloctanoic acid, a salt thereof or a prodrug thereof wherein the amount per dose is from 1 mg to 5000 mg (preferably from 10 mg to 5000 mg), is highly safe and can remarkably relieve a pain, in particular, a neurogenic pain associated with a disease such as cancer pain, postherpetic pain, diabetic pain, HIV-associated neurogenic pain, calculus-induced pain, neuralgia, orofacial pain or hyperalgesia. Thus, the degree of freedom in the patient's life can be elevated and the QOL can be improved. Additionally, it can suppress the dependency of an analgesic (in particular, an opioid analgesic) or tolerance thereto; reduce the amount of an analgesic employed; and retard the starting point of using an analgesic or relieve the side effect, which makes it useful as a medicine.

The invention claimed is:
1. A method of treating neurogenic pain in a mammal suffering from neurogenic pain, said method comprising administering (2R)-2-propyloctanoic acid or a pharmaceutically acceptable salt thereof to said mammal in need thereof, wherein said (2R)-2-propyloctanoic acid or a pharmaceutically acceptable salt thereof is administering in an amount of from 10 mg to 5000 mg per dose, and wherein the neurogenic pain is selected from the group consisting of postherpetic pain, diabetic pain, HIV-associated neurogenic pain, calculus-induced pain, neuralgia, orofacial pain and hyeralgesia.

2. The method according to claim 1, wherein the administration is oral administration in an amount of from 100 mg to 5000 mg per dose.

3. The method according to claim 1, wherein the administration is parenteral administration.

4. The method according to claim 3, wherein the parenteral administration is intravenous administration.

5. The method according to claim 4, wherein the amount per dose in the intravenous administration is from 100 mg to 2000 mg.

6. The method according to claim 4, wherein the amount per dose in the intravenous administration is from 2 mg to 20 mg per 1 kg of body weight.

7. The method according to claim 4, wherein the intravenous administration is intravenous drip infusion.

\* \* \* \* \*